United States Patent [19]
Choksi

[11] Patent Number: 5,286,067
[45] Date of Patent: * Feb. 15, 1994

[54] TAPER FITTING WITH PROTECTIVE SKIRT

[76] Inventor: Pradip Choksi, 9614-F Cozycroft Ave., Chatsworth, Calif. 91311

[*] Notice: The portion of the term of this patent subsequent to Jan. 5, 2010 has been disclaimed.

[21] Appl. No.: 923,746

[22] Filed: Jul. 29, 1992

Related U.S. Application Data

[63] Continuation-in-part of Ser. No. 568,090, Aug. 16, 1990, Pat. No. 5,176,415.

[51] Int. Cl.$^5$ .................................................. F16L 35/00
[52] U.S. Cl. ........................................ 285/38; 285/93; 285/331; 285/332; 285/353; 285/423; 285/901; 285/906
[58] Field of Search ............... 285/32, 33, 330, 332.1, 285/332.2, 331, 901, 423, 38, 93, 332, 353, 906

[56] References Cited

U.S. PATENT DOCUMENTS

| | | | |
|---|---|---|---|
| 2,962,688 | 11/1960 | Werner | 285/901 X |
| 3,427,707 | 12/1965 | Nowosadko . | |
| 3,633,586 | 1/1972 | Sheridan . | |
| 3,752,510 | 2/1973 | Windischman et al. . | |
| 3,902,489 | 9/1975 | Carter . | |
| 3,976,311 | 8/1976 | Spendlove | 285/901 X |
| 3,986,508 | 10/1976 | Barrington . | |
| 4,046,479 | 2/1977 | Paley . | |
| 4,187,846 | 2/1980 | Lolachi et al. . | |
| 4,201,208 | 5/1980 | Cambio . | |
| 4,201,406 | 5/1980 | Dinnehey et al. . | |
| 4,254,773 | 3/1981 | Waldbillig . | |
| 4,266,815 | 5/1981 | Cross . | |
| 4,296,949 | 10/1981 | Muetterties et al. . | |
| 4,326,569 | 4/1982 | Vaillancourt . | |
| 4,369,781 | 1/1983 | Gilson et al. . | |
| 4,452,473 | 6/1984 | Ruschke . | |
| 4,508,367 | 4/1985 | Orcopoulos et al. . | |
| 4,511,359 | 4/1985 | Vaillancourt . | |
| 4,538,836 | 9/1985 | Krutten . | |
| 4,566,480 | 1/1986 | Parham . | |
| 4,607,868 | 8/1986 | Harvey et al. . | |
| 4,610,469 | 9/1986 | Wolf-Mooij . | |
| 4,634,027 | 1/1987 | Kanarvogel . | |
| 4,639,019 | 1/1987 | Mittleman . | |
| 4,649,904 | 3/1987 | Krauter et al. . | |
| 4,653,539 | 3/1987 | Bell . | |
| 4,676,530 | 6/1987 | Nordgren et al. . | |
| 4,693,710 | 9/1987 | McCool . | |
| 4,704,177 | 11/1987 | Vaillancourt . | |
| 4,735,441 | 4/1988 | Stephen . | |
| 4,737,334 | 4/1988 | Folding et al. . | |
| 4,801,296 | 1/1989 | Vaillancourt . | |
| 4,919,167 | 4/1990 | Manska . | |
| 4,929,235 | 5/1990 | Merry et al. . | |
| 4,932,114 | 6/1990 | Morse et al. . | |

Primary Examiner—Dave W. Arola
Attorney, Agent, or Firm—Stetina and Brunda

[57] ABSTRACT

A shrouded tubing interface for quickly connecting, disconnecting and avoiding contamination of first and second fluid flow lines comprising male and female connectors, each of which are connected to a respective one of the fluid flow lines. The male connector includes a first tubular portion defining a distal tip and a tapered outer surface, while the female connector includes a second tubular portion having a distal tip and a tapered inner surface. The tapered surfaces of the first and second tubular portions are mutually tapered such that the first and second tubular portions are axially interfittable. The male and female connectors further include first and second tubular skirt portions, respectively, associated with and extending about the respective tubular portions which are adapted to prevent contact to respective ones of the distal ends, and are further positioned to radially and axially overlap when the tubular portions are brought into interfitting engagement at the tapering surfaces.

18 Claims, 3 Drawing Sheets

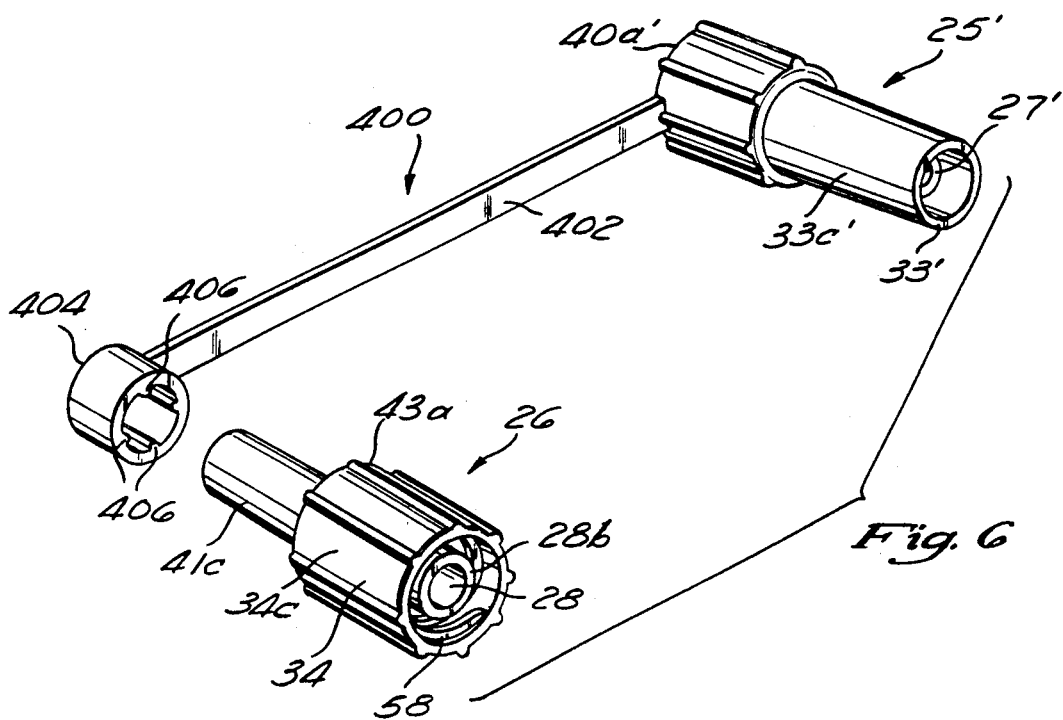
Fig. 6
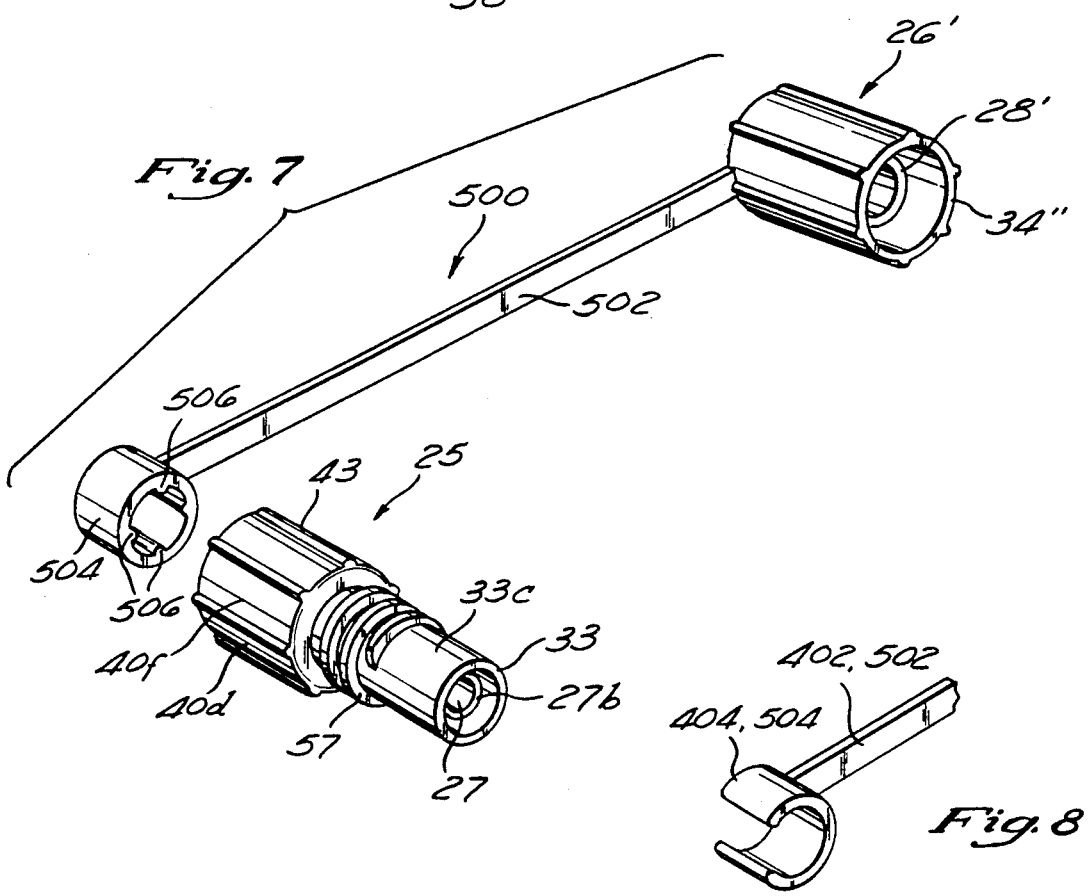
Fig. 7
Fig. 8

TAPER FITTING WITH PROTECTIVE SKIRT

FIELD OF THE INVENTION

The present application is a continuation-in-part of application Ser. No. 07/568,090 filed Aug. 16, 1990, are now U.S. Pat. No. 5,176,415 issued Jan. 15, 1993, the disclosure of which is incorporated herein by reference. The present invention relates generally to fittings used in connecting tubings, and more particularly, to taper fittings with protective skirts for use in medical applications for purposes of quickly connecting, disconnecting and avoiding contamination of first and second fluid flow lines.

BACKGROUND OF THE INVENTION

In hospitals, taper fittings are commonly used to connect tubings carrying intravenous fluids, blood and medications. One of the most commonly used taper fittings is referred to as a luer. Typically, a luer comprises a small diameter fitting incorporating a through hole having a diameter of approximately 1/16 inch. The male luer fitting is often provided with a skirt having internal threads. The matching female luer has locking ears or external threads to facilitate a secure connection to the male luer. FIG. 1 illustrates prior art male and female luers with locking threads. In the prior art luer shown in FIG. 1, the female luer has no skirt, while the tip of the male luer extends beyond the threaded skirt included therewith.

One of the deficiencies associated with the prior art luer fitting is that when the fitting is disconnected, fluid such as blood that is flowing through the tubing can be easily touched by the person disconnecting the fittings. As will be recognized, such exposure compromises the sterility of the system since the touching of the tips of the luer fittings introduces contaminants into the system in addition to exposing the person coming into contact with the body fluids to infectious diseases such as hepatitis or AIDS.

As such, there exists a need in the art for a simple, effective means to protect such fittings and tubing connections against contamination. The present invention overcomes the deficiencies associated with the prior art luer fittings by providing a shrouded tubing interface for quickly connecting, disconnecting and avoiding contamination of first and second fluid flow lines.

SUMMARY OF THE INVENTION

In accordance with a preferred embodiment of the present invention, there is provided a shrouded tubing interface for quickly connecting, disconnecting and avoiding contamination of first and second fluid flow lines. The device generally comprises a male connector which is fluidly connected to a first fluid flow line and a female connector which is fluidly connected to a second fluid flow line. In the preferred embodiment, the male connector comprises a first tubular portion which is in fluid communication with the first flow line and defines a distal tip and a tapered outer surface. Disposed about and spaced radially from the outer surface of the first tubular portion is a first tubular skirt portion which has inner and outer surfaces and is sized to extend axially beyond the first distal tip of the first tubular portion to prevent inadvertent contact to and contamination of the first distal tip.

In the preferred embodiment, the female connector comprises a second tubular portion which is in fluid communication with the second fluid flow line and defines a second distal tip and a tapered inner surface which is complementary to the tapered outer surface of the first tubular portion. Disposed about and spaced radially from the second tubular portion is a second tubular skirt portion which has inner and outer surfaces and is sized to extend axially beyond the second distal tip of the second tubular portion to prevent inadvertent contact to and contamination of the second distal tip.

The male connector is fluidly connected to the female connector via the receipt of the first distal tip and a portion of the first tubular portion into the second distal tip of the second tubular portion. Additionally, the first tubular portion is maintained in sealed engagement to the second tubular portion via the releasable connection of the first skirt portion to the second skirt portion. When connected to each other, the first and second skirt portions extend in concentric, coaxial relation. In the preferred embodiment, the first tubular skirt portion includes male threads formed about a portion of the outer surface thereof, while the second tubular skirt portion includes female threads formed within a portion of the inner surface thereof. In this respect, the releasable connection of the first and second tubular skirt portions to each other is facilitated by the threadable engagement of the male threads to the female threads.

The male connector further includes a first sleeve portion for telescopically receiving the first fluid flow line while the female connector further includes a second sleeve portion for telescopically receiving the second fluid flow line. As an alternative to the first and second sleeve portions, the male and female connectors may include first and second barbed portions, respectively, which are adapted to be received into and frictionally retained within a respective fluid flow line. Disposed about and spaced from the first sleeve portion of the male connector is a first grip portion. In the preferred embodiment, the outer surfaces of the first grip portion and the second tubular skirt portion include grip edges formed thereabout for aiding in the connection of the male connector to the female connector. Additionally, the second tubular skirt portion may be rotatably attached to the female connector for allowing the female threads to be threadably engaged to the male threads without rotating the second tubular portion thereof. Both the male and female connectors are preferably fabricated from a translucent material, though other materials may be utilized as an alternative.

The male connector may further comprise an elongate tether member having a proximal end rigidly attached to the first grip member thereof and a distal end rigidly attached to the second fluid flow line adjacent the second sleeve portion of the female connector. Advantageously, the tether member is operable to maintain the first flow line in close proximity to the second flow line when the male connector is disconnected from the female connector. Disposed on the distal end of the tether member is a loop member which is used to frictionally receive a portion of the second fluid flow line. Additionally, the proximal end of the tether member may be pivotally connected to the first grip member.

As an alternative to being attached to the male connector, the proximal end of the tether member may be rigidly attached to the second tubular skirt portion of the female connector, with the distal end being rigidly attached to the first fluid flow line adjacent the first sleeve portion of the male connector. The tether member attached to the female connector, like that attached to the male connector, also includes a loop member disposed on the distal end thereof for receiving a portion of the first fluid flow line and may be pivotally connected to the second tubular skirt portion of the female connector.

Advantageously, the present invention eliminates touch contamination of aseptic fluid paths and reduces the risk of health care workers coming in contact with infectious fluids, while maintaining currently used connect/disconnect techniques for taper fittings. Additionally, the rotatable connection of the second tubular skirt portion to the female connector provides twist-free connection and disconnection of the female connector to the male connector, while the pivotal connection of the proximal end of the tether member to either the first grip portion or second tubular skirt portion also prevents the twisting of the first or second fluid flow lines during the connection and disconnection of the male and female connectors. The fabrication of the male and female connectors from a translucent material permits visualization of the tapered interface of the first tubular portion to the second tubular portion, while the inclusion of the grip edges or ribs upon the outer surfaces of the first grip portion and second tubular skirt portion provide a firm grip for the connection and disconnection of the male and female connectors. Further, the male and female connectors are designed for either an adhesive bond or barbed gripping to the first and second fluid flow lines.

BRIEF DESCRIPTION OF THE DRAWINGS

These as well as other features of the present invention will become more apparent upon reference to the drawings wherein:

FIG. 6 is a perspective view of a male connector constructed in accordance with a fourth embodiment of the present invention including a tether member attached thereto; and FIG. 7 is a perspective view of a female connector constructed in accordance with a fifth embodiment of the present invention including a tether member attached thereto.

FIG. 8 is a perspective view of a modification of the loop member.

DETAILED DESCRIPTION OF THE PREFERRED EMBODIMENT

Figure 1:
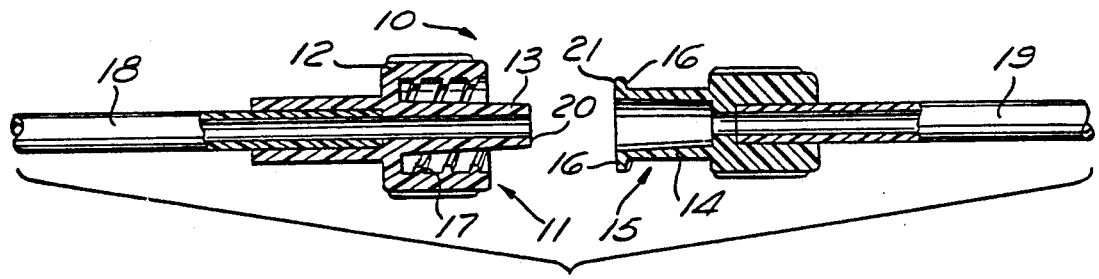
FIG. 1 is a cross-sectional view of a prior art luer fitting.

Referring now to the drawings wherein the showings are for purposes of illustrating preferred embodiments of the present invention only, and not for purposes of limiting the same, FIG. 1 illustrates a prior art fitting 10. Fitting 10 generally comprises a male luer 11 having a skirt 12 and a stem 13. The stem 13 is received into a receptacle 14 of a female luer 15 which has ears 16 that engage threads 17 in the skirt 12. Fluidly connected to the male luer 11 is a first flexible tubing 18, while fluidly connected to the female luer 15 is a second flexible tubing 19.

As seen in FIG. 1, the distal end of the stem 13 of the male luer 11 defines an unprotected surface 20, while the distal end of the receptacle 14 of the female luer 15 defines an unprotected surface 21. As will be recognized, when the male luer 11 and female luer 15 are in disconnected relation, the unprotected surfaces 20 and 21 may become moistened with a body fluid and thus be contaminated. Additionally a doctor, nurse or other hospital attendant, who handles the fitting 10 by connecting or disconnecting the same, can easily touch the unprotected surfaces 20 and 21, thereby becoming exposed to such contamination.

Figure 2:
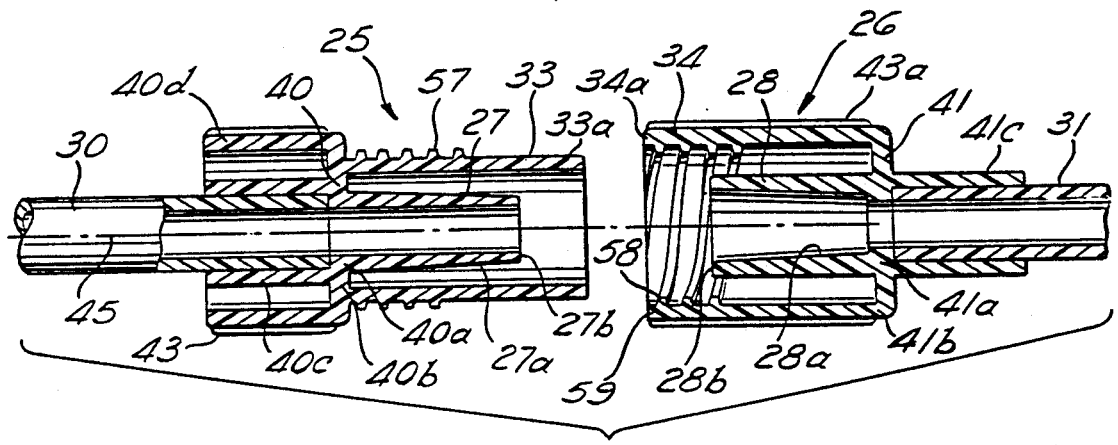
FIG. 2 is a cross-sectional view of a first embodiment of the male and female connectors of the present invention in disconnected relation.
Figure 2A:
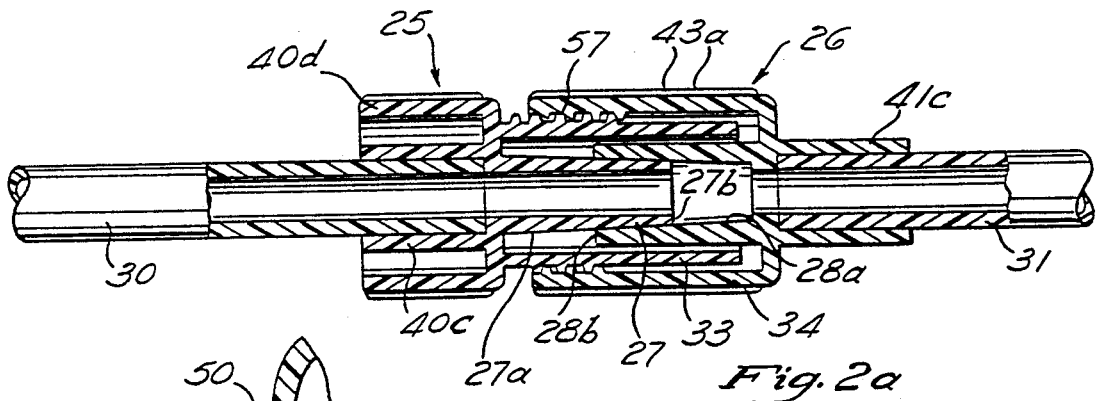
FIG. 2a is a cross-sectional view illustrating the male and female connectors of FIG. 2 in connected relation.
Figure 3:
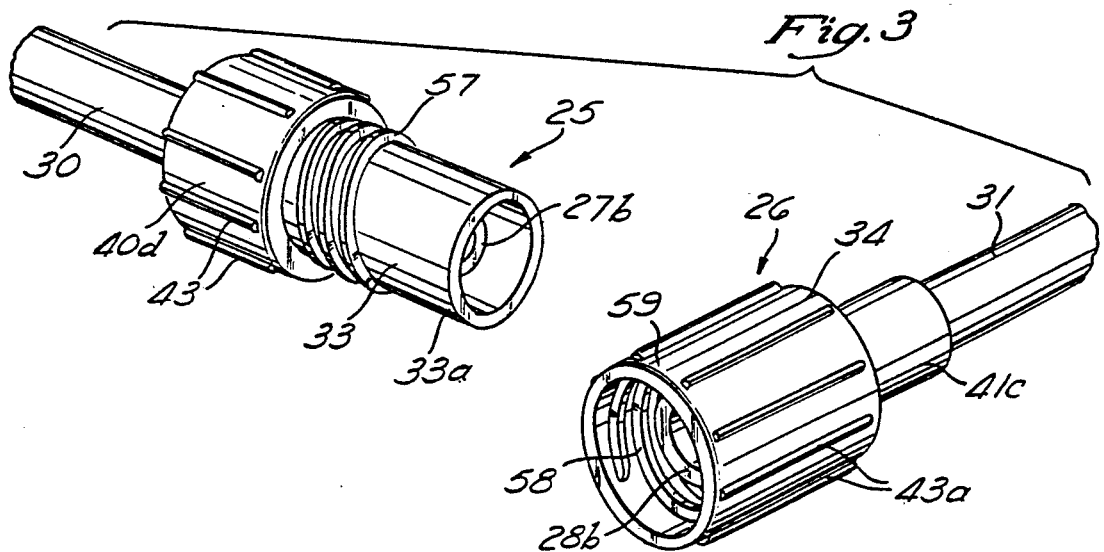
FIG. 3 is a perspective view of the male and female connectors shown in FIG. 2 in disconnected relation.

Referring now to FIGS. 2, 2a and 3, disclosed is a shrouded tubing interface or fitting 22 constructed in accordance with a first embodiment of the present invention. The fitting 22 generally comprises a male connector 25 and a female connector 26. Male connector 25 is fluidly connected to a first tubular fluid flow line 30, while female connector 26 is fluidly connected to a second tubular fluid flow line 31. The flow lines 30 and 31 may be fabricated from materials which are flexible and/or transparent.

In the first embodiment, male connector 25 comprises a first tubular portion 27 which is in fluid communication with the first fluid flow line 30 and defines a distal tip 27b and an elongate, tapered outer surface 27a. Disposed about and spaced radially outwardly from the outer surface 27a of the first tubular portion 27 is a first tubular skirt portion 33 having an inner surface 33b and an outer surface 33c. Importantly, first tubular skirt portion 33 is sized to extend axially beyond the first distal tip 27b of first tubular portion 27 as indicated by end extent 33a of the first tubular skirt portion 33. As will be recognized, sizing the first tubular skirt portion 33 to extend axially beyond the first distal tip 27b prevents inadvertent contact to and contamination of the first distal tip 27b.

Female connector 26 comprises a second tubular portion 28 which is in fluid communication with the second fluid flow line 31 and defines a second distal tip 28b and an elongate, tapered inner surface 28a which is complementary to the tapered outer surface 27a of first tubular portion 27. As can be appreciated, the tapers of the outer surface 27a and inner surface 28a are matching and sufficiently shallow, as in a luer fitting, such that surface interengagement friction tends to maintain the first tubular portion 27 within the second tubular portion 28 when such is inserted thereinto. However, it will be recognized that the outer surface 27a and inner surface 28a need not necessarily be tapered for the first tubular portion 27 and the second tubular portion 28 to be axially interfittable. Disposed about and spaced radially outwardly from the second tubular portion 28 is a second tubular skirt portion 34 having an inner surface 34b and an outer surface 34c. Similar to the first tubular skirt portion 33, second tubular skirt portion 34 is sized to extend axially beyond the second distal tip 28b of second tubular portion 28 as indicated by the end extent 34a of second tubular skirt portion 34. Advantageously, the sizing of the second tubular skirt portion 34 to extend axially beyond the second distal tip 28b prevents inadvertent contact to and contamination of the second distal tip 28b.

As previously indicated, the male connector 25 is fluidly connected to the female connector 26 via the receipt of the first distal tip 27b and first tubular portion 27 thereof into the second distal tip 28b and second tubular portion 28 of the female connector 26. Though the first tubular portion 27 is frictionally retained within the second tubular portion 28 due to the mutually tapering configurations, the first tubular portion 27 is maintained in sealed engagement to the second tubular portion 28 via the releasable connection of the first tubular skirt portion 33 to the second tubular skirt portion 34. As seen in FIG. 2a, when the first tubular portion 27 is received into the second tubular portion 28, the first tubular skirt portion 33 and the second tubular skirt portion 34 extend in coaxial and concentric relation. In the first embodiment, the second tubular skirt portion 34 is sized to be extensible over and overlap the first tubular skirt portion 33.

As best seen in FIGS. 2 and 2a, the first tubular skirt portion 33 is joined to the first tubular portion 27 via a first tubular body structure 40 which is integral with the first tubular portion 27. Similarly, the second tubular skirt portion 34 is joined to the second tubular portion 28 via a second tubular body structure 41 which is integral with the second tubular portion 28. The first tubular body structure 40 merges with the end of first tubular portion 27 closest to first fluid flow line 30 at 40a, while second tubular body structure 41 merges with the end of second tubular portion 28 closest to the second fluid flow line 31 at 41a. Additionally, the first tubular body structure 40 merges with the end of first tubular skirt portion closest to first fluid flow line 30 at 40b, while second tubular body structure 41 merges with the end of second tubular skirt portion 34 closest second fluid flow line 31 at 41b.

Projecting outwardly from first tubular body structure 40 is a first sleeve portion 40c which is sized to telescopically receive and interfit the end of first fluid flow line 30 in a manner placing first fluid flow line 30 in the fluid communication with first tubular portion 27. Additionally, projecting outwardly from second tubular body structure 41 is a second sleeve portion 41c which is sized to telescopically receive and interfit the end of second fluid flow line 31 in a manner placing second fluid flow line 31 in fluid communication with the second tubular portion 28. Disposed about and spaced radially outwardly of first sleeve portion 40c is a first tubular grip portion 40d which projects outwardly from first tubular body structure 40 and defines an inner surface 40e and an outer surface 40f. In the first embodiment, the ends of the first and second fluid flow lines 30 and 31 are preferably maintained within the respective sleeve portions 40c and 41c via a bonding process, such as through the use of an adhesive. Formed about the outer surface 40f of first grip portion 40d are grip edges 43, such as ribs, which are spaced about the axis 45 of the fitting 22. Additionally, disposed about the outer surface 34c of second tubular skirt portion 34 are grip edges 43a which also are spaced about the axis 45. The grip edges or ribs 43 and 43a are used to aid the manual grasping of the male connector 25 and female connector 26 during the connection and disconnection of the same.

Figure 2B:
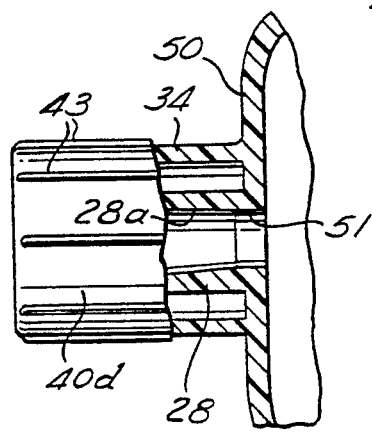
FIG. 2b is a partial cross-sectional view of an embodiment of the invention wherein a female connector is integrally formed as part of a bottle.

Referring now to FIG. 2b, the female connector 26 may be formed integral with a bottle 50. In this respect, the second tubular body structure 41 of the female connector 26 is merged with the wall of the bottle 50 with the tubular extent 51 being considered a flow line. Additionally, though not shown, the male connector 25 may also be made integral with a structure such as the bottle 50. In the first embodiment, the male connector 25 and female connector 26, including the first and second tubular portions 27 and 28, first and second tubular skirt portions 27 and 28 and first and second tubular body structures 40 and 41 may be fabricated from a molded plastic material that may be transparent for allowing the viewing of the flow of fluid through the fitting 22.

As shown in FIGS. 2 and 2a, the male connector 25 and female connector 26 preferably include interengageable threads to retain them in fluid connection to each other when the first tubular portion 27 is received into and brought into sealed engagement with the second tubular portion 28. In this respect, formed on the outer surface 33c of first tubular skirt portion 33 about the inner extent 57a thereof are male threads 57, while formed in the inner surface 34b of second tubular skirt portion 34 about the outer extent 59 thereof are female threads 58. As will be recognized, the threadable engagement of the male threads 57 to the female threads 58 serves to releasably connect the first and second tubular skirt portions 33 and 34 to each other in the manner shown in FIG. 2a.

Figure 4:
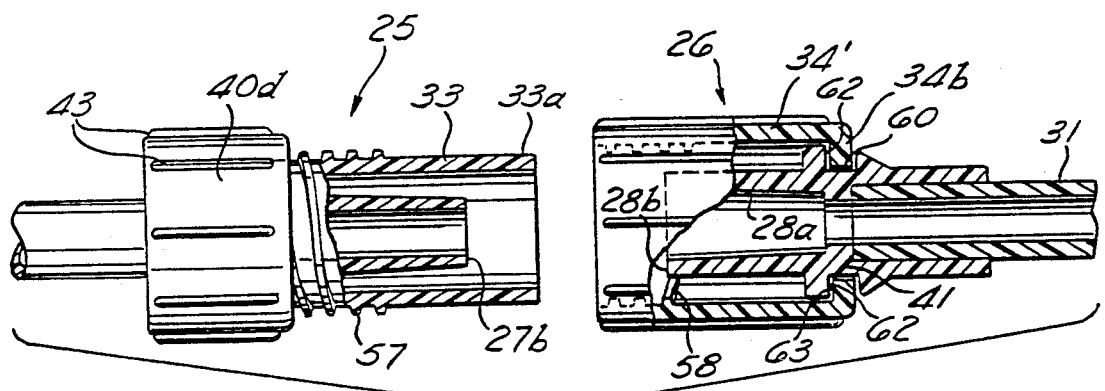
FIG. 4 is a partial cross-sectional view of the male connector in disconnected relation to a female connector constructed in accordance with a second embodiment of the present invention.

Referring now to FIG. 4, illustrated is a fitting 100 constructed in accordance with a second embodiment of the present invention. Fitting 100 includes the male connector 25 as previously discussed with respect to the first embodiment. Also included is a female connector 26a which differs from the female connector 26 previously described in that the female connector 26a of the second embodiment includes a second tubular skirt portion 34' which is adapted to be rotatable relative the second tubular portion 28 about the axis defined by the second tubular portion 28. In this respect, the second tubular skirt portion 34' includes an annular flange portion 34b which is received into an annular groove 60 defined within the body structure 41. The receipt of the flange 34b into the groove 60 allows relative annular rotation of the skirt portion 34' and body structure 41 relative the second tubular portion 28 during the engagement of the female connector 26a to the male connector 25. As can be appreciated, the rotation of the second tubular skirt portion 34' allows the female threads 58 disposed therein to be threadably engaged to the male threads 57 of the male connector 25 without the necessity of having to twist either the first or second fluid flow lines 30 and 31. Additionally, the tightening of the female threads 58 against the male threads 57 during the connection of the female connector 26 to the male connector 25 causes the surface 63 to be firmly abutted against the surface 62.

Figure 5:
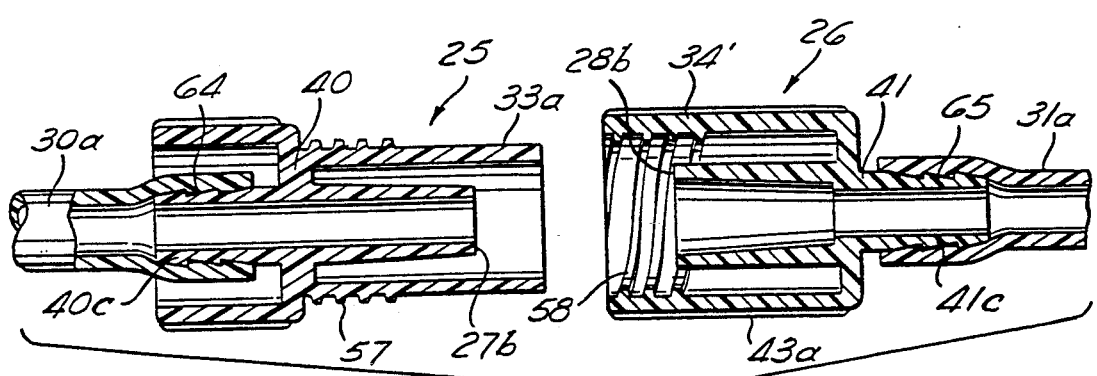
FIG. 5 is a cross-sectional view of male and female connectors constructed in accordance with a third embodiment of the present invention, in disconnected relation.

Referring now to FIG. 5, illustrated is a fitting 200 constructed in accordance with a third embodiment of the present invention. Fitting 200 includes a male connector 25a which is identically configured to the male connector 25 previously described with respect to the first embodiment, except that the outer surface of the first sleeve portion 40c is formed to include barbed interfits 64. Additionally, the female connector 26b of fitting 200 is identically configured to the female connector 26 previously described with respect to the first embodiment, except that the outer surface of the second sleeve portion 41c is likewise provided with barbed interfits 65. In the third embodiment, the barbed interfits 64 and 65 are adapted to allow the first sleeve portion 40c and second sleeve portion 41c to be received into and frictionally retained within the first and second fluid flow lines 30 and 31, respectively.

Referring now to FIG. 6, illustrated is a male cap member 400 which may be used in conjunction with and is selectively attachable to the female connector 26 previously described with respect to the first embodiment for purposes of preventing the contamination of the second tubular portion 28 when the female connector 26 is disconnected from the male connector 25. Cap member 400 includes a male portion 25' which is similarly configured to the male connector 25 previously described with respect to the first embodiment, except that male portion 25' does not include the male threads 57 formed about the outer surface 33c' of the first tubular skirt portion 33' thereof. Additionally, the lumen of the first tubular portion 27' does not extend longitudinally through the entire male portion 25' since the male cap member 400 is not adapted to have fluid flow therethrough. As such, the first tubular portion 27' may alternatively be configured as a solid member defining a tapered outer surface. Rigidly attached to and extending from the first grip portion 40d' of male portion 25' is an elongate tether member 402. Disposed on the distal end of tether member 402 is a loop member 404 including a plurality of crush grips 406 formed about the inner surface thereof.

In the male cap member 400, the loop member 404 is adapted to receive a portion of the outer surface of the second sleeve portion 41c of female connector 26 for purposes of maintaining the male portion 25' in close proximity to the female connector 26. The loop member 404 is rigidly maintained in position on the outer surface of the second sleeve portion 41c via the crushing of the ribs 406 when the loop member 404 is positioned upon the second sleeve portion 41c. As an alternative to incorporating the loop member 404, the distal end of the tether member 402 may be rigidly attached to the second sleeve portion 41c by any suitable method. As will be recognized, the loop member 404 may be engaged to the second sleeve portion 41c prior to the insertion of the second fluid flow line 31 thereinto, thus allowing the female connector 26 and corresponding male cap member 400 to be provided as a single unit. When the female connector 26 is disconnected from the male connector 25, the male portion 25' is engaged to the female connector 26 in a manner wherein the first tubular portion 27' is received into and brought into sealed engagement with the second tubular portion 28, with the first tubular skirt portion 33' being axially overlapped by the second tubular skirt portion 34.

Though the male portion 25' as shown in FIG. 6 does not include male threads 57 and the female connector 26 is provided with the female threads 58, it will be recognized that the male portion 25' may be formed to include male threads on the outer surface 33c' of first tubular skirt portion 33' to engage the female threads 58 of female connector 26. In the event the second tubular skirt portion 34 of the female connector 26 is non-rotating and the male portion 25' provided with male threads, it is contemplated that the proximal end of the tether member 402 may be pivotally attached to the first grip portion 40d' so as to prevent the twisting of the tether member 402 and second fluid flow line 31 when the male portion 25' is threadably engaged to the female connector 26. As an alternative to pivotally attaching the proximal end of the tether member 402 to the first grip portion 40d', the loop member 404 may be rotatably engaged to the outer surface of the second sleeve portion 41c by eliminating the ribs 406 from therewithin, thus allowing the loop member 404 to be "free spinning" about the second sleeve portion 41c. Additionally, as seen in FIG. 8, the loop member 404 may be provided with a slot 600 extending axially therethrough, thus giving the loop member 404 a generally C-shaped configuration to allow it to be rotatably connected to the second sleeve portion 41c by snap-fitting it onto the outer surface thereof.

Referring now to FIG. 7, disclosed is a female cap member 500 which may be used in conjunction with and is selectively attachable to the male connector 25 previously discussed with respect to the first embodiment for purposes of preventing the contamination of the first tubular portion 27 when the male connector 25 is disconnected from the female connector 26. Cap member 500 includes a female portion 26' which is similarly configured to the female connector 26 previously described with respect to the first embodiment, except that rigidly attached to and extending from the second tubular skirt portion 34" of female portion 26' is an elongate tether member 502. Additionally, the lumen of the second tubular portion 28' does not extend longitudinally through the entire female portion 26' since the female cap member 500 is not adapted to have fluid flow therethrough. Disposed on the distal end of tether member 502 is a loop member 504 including a plurality of crush ribs 506 formed about the inner surface thereof.

In the female cap member 500, the loop member 504 is adapted to receive a portion of the outer surface of the first tubular portion 40c of male connector 25. The loop member 504 is maintained in rigid engagement to the outer surface of the first tubular portion 40c via the crushing of the ribs 506 when the loop member 504 is positioned about the first tubular portion 40c. Similar to the tether member 402 previously described, the tether member 502 maintains the female portion 26' in close proximity to the male connector 25. As will be recognized, the loop member 504 may be engaged to the first sleeve portion 40c prior to the insertion of the first fluid flow line 30 thereinto, thus allowing the male connector 25 and corresponding female cap member 500 to be provided as a single unit. When the male connector 25 is disconnected from the female connector 26, the female portion 26' is engaged to the male connector 25 in a manner wherein the first tubular portion 27 is received into and brought into sealed engagement with the second tubular portion 28', with the first tubular skirt portion 33 being axially overlapped by the second tubular skirt portion 34".

Though the male connector 25 as shown in FIG. 7 is provided with male threads 57 and the female portion 26' does not include female threads disposed within the second tubular skirt portion 34", it will be recognized that female connector 26' may be provided with female threads within the second tubular skirt portion 34" to engage the male threads 57 of male connector 25. In the event the tubular skirt portion 34" of the female portion 26' is provided with female threads, it is contemplated that the proximal end of the tether member 502 may be pivotally connected to the second tubular skirt portion 34" of the female portion 26' to prevent the twisting of the tether member 502 and first fluid flow line 30 when the female portion 26' is threadably engaged to the male connector 25. As an alternative to pivotally attaching the proximal end of the tether member 502 to the second tubular skirt portion 34", the loop member 504 may be rotatably engaged to the outer surface of the first sleeve portion 40c by eliminating the ribs 506 from therewithin, thus allowing the loop member 504 to be "free spinning" about the first sleeve portion 40c. Additionally, as also seen in FIG. 8, the loop member 504 may be provided with a slot 600 extending axially therethrough, thus giving the loop member 504 a generally C-shaped configuration to allow it to be rotatably connected to the first sleeve portion 40c by snap-fitting it onto the outer surface thereof.

It is contemplated that the fittings as previously described with respect to the various embodiments of the present invention may be used for a number of applications including intravenous therapy involving the connection of an intravenous catheter to an intravenous set or the connection of extension tubing to an intravenous set or catheter; blood infusion involving the connection of a blood infusion set to a catheter; wound drainage involving the connection of a wound drain tube to an evacuation container; autotransfusion involving the connection of a drain tube to a collection container; chest drainage involving the connection of a chest drainage tube to a catheter or a collection container; urology involving the connection of a Foley catheter to a drainage tube and/or the connection of a urine bag emptying port to a collection receptacle; suctioning involving the connection of a suction catheter to a suction line; or other applications.

Additional modifications and improvements of the present invention may also be apparent to those skilled in the art. Thus, the particular combination of parts described and illustrated herein is intended to represent only certain embodiments of the invention, and is not intended to serve as limitations of alternative devices within the spirit and scope of the invention.

What is claimed is:

1. A shrouded tubing interface for quickly connecting, disconnecting and avoiding contamination of first and second fluid flow lines, comprising:
   a male connector fluidly connected to said first fluid flow line, said male connector comprising:
   (a) a first tubular portion defining a distal tip and a tapered outer surface, said first tubular portion being in fluid communication with said first flow line; and
   (b) a first tubular skirt portion disposed about and spaced from the outer surface of said first tubular portion, said first skirt portion having inner and outer surfaces and being sized to extend axially beyond the first distal tip of said first tubular portion to prevent inadvertent contact to and contamination of said first distal tip;
   a female connector fluidly connected to said second fluid flow line, said female connector comprising:
   (a) a second tubular portion defining a second distal tip and a tapered inner surface complementary to the tapered outer surface of said first tubular portion, said second tubular portion being in fluid communication with said second flow line; and
   (b) a second tubular skirt portion disposed about and spaced from said second tubular portion, said second skirt portion having inner and outer surfaces and being sized to extend axially beyond the second distal tip of said second tubular portion to prevent inadvertent contact to and contamination of said second distal tip;
   said male connector being fluidly connected to and maintained in sealed engagement with said female connector via the receipt of the first distal tip and said first tubular portion into the second distal tip of said second tubular portion, said first and second skirt portions extending in concentric, co-axial relation when said first tubular portion is received into said second tubular portion.

2. The device of claim 1 wherein said first tubular skirt portion includes male threads formed about a portion of the outer surface thereof and said second tubular skirt portion includes female threads formed within a portion of the inner surface thereof, said male threads being engageable to said female threads to prevent said first tubular portion from being pulled out of said second tubular portion.

3. The device of claim 2 wherein said second tubular skirt portion is rotatably attached to said female connector for allowing said female threads to be threadably engaged to said male threads without rotating said second tubular portion.

4. The device of claim 2 wherein said male connector further includes a first sleeve portion for telescopically receiving said first fluid flow line and said female connector further includes a second sleeve portion for telescopically receiving said second fluid flow line.

5. The device of claim 4 wherein said male connector further includes a first grip portion disposed about and spaced from said first sleeve portion, said first grip portion having inner and outer surfaces.

6. The device of claim 5 further comprising a plurality of grip edges formed about the outer surface of said first grip portion and about the outer surface of said second tubular skirt portion for aiding in the connection of said male connector to said female connector.

7. The device of claim 4 further comprising a male cap member selectively attachable to said female connector when said female connector is disconnected from said male connector, said male cap member comprising:
   a male portion including a tubular portion defining a distal tip and a tapered outer surface, and a tubular skirt portion disposed about and spaced from the outer surface of said tubular portion, said tubular skirt portion having inner and outer surfaces and being sized to extend axially beyond the distal tip of said tubular portion; and
   an elongate tether member having a proximal end rigidly attached to said tubular skirt portion and a distal end rigidly attached to said second fluid flow line adjacent said second sleeve portion, said tether member being operable to maintain said male portion in close proximity to said female connector;
   said tubular portion being received into and brought into sealed engagement with said second tubular portion and said tubular skirt portion being axially overlapped by said second tubular skirt portion when said male portion is engaged to said female connector.

8. The device of claim 7 wherein said tether member includes a loop member disposed on the distal end thereof for receiving a portion of said second sleeve portion.

9. The device of claim 8 wherein the loop member is rotatably connected to the second sleeve portion.

10. The device of claim 9 wherein said male portion further includes male threads formed on the outer surface of said tubular skirt portion for threadably engaging the female threads disposed within the inner surface of said second tubular skirt portion.

11. The device of claim 10 wherein the loop member has a generally C-shaped configuration.

12. The device of claim 4 further comprising a female cap member selectively attachable to said male connector when said male connector is disconnected from said female connector, said female cap member comprising:
a female portion including a tubular portion defining a distal tip and a tapered inner surface complementary to the tapered outer surface of said first tubular portion, and a tubular skirt portion disposed about and spaced from said tubular portion, said tubular skirt portion having inner and outer surfaces and being sized to extend axially beyond the distal tip of said tubular portion; and
an elongate tether member having a proximal end rigidly attached to said tubular skirt portion and a distal end rigidly attached to said first fluid flow line adjacent said first sleeve portion, said tether member being operable to maintain said female portion in close proximity to said male connector;

said first tubular portion being received into and brought into sealed engagement with said tubular portion and said first tubular skirt portion being axially overlapped by said tubular skirt portion when said female portion is engaged to said male connector.

13. The device of claim 12 wherein said tether member includes a loop member disposed on the distal end thereof for receiving a portion of said first sleeve portion.

14. The device of claim 13 wherein the loop member is rotatably connected to the first sleeve portion.

15. The device of claim 14 wherein said female portion further includes female threads disposed within the inner surface of said tubular skirt portion for threadably engaging the male threads of said male connector.

16. The device of claim 15 wherein the loop member has a generally C-shaped configuration.

17. The device of claim 1 wherein said male connector further includes a first barbed portion adapted to be received into and frictionally retained within said first fluid flow line and said female connector includes a second barbed portion adapted to be received into and frictionally retained within said second fluid flow line.

18. The device of claim 1 wherein said male connector and said female connector are fabricated from a translucent material.

* * * * *